United States Patent [19]
Radke

[11] Patent Number: 4,595,010
[45] Date of Patent: Jun. 17, 1986

[54] ELECTRICAL MUSCLE STIMULATOR

[75] Inventor: John C. Radke, Whitefish Bay, Wis.

[73] Assignee: Bio-Research Associates, Inc., Milwaukee, Wis.

[21] Appl. No.: 588,379

[22] Filed: Mar. 12, 1984

[51] Int. Cl.$^4$ ............................................. A61N 1/36
[52] U.S. Cl. ................................................. 128/421
[58] Field of Search .............................. 128/421–423

[56] References Cited

U.S. PATENT DOCUMENTS

| Re. 27,847 | 12/1973 | Jankelson | 433/140 |
|---|---|---|---|
| D. 249,550 | 9/1978 | Jankelson et al. | D24/36 |
| 409,437 | 8/1889 | Vernette | 128/791 |
| 467,738 | 1/1892 | Horton, Jr. | 128/791 |
| 1,487,998 | 3/1924 | Woolf | 128/791 |
| 2,842,136 | 7/1958 | Browner | 128/422 |
| 3,180,338 | 4/1965 | Moss et al. | 128/422 |
| 3,387,147 | 6/1968 | Radwan | 307/275 |
| 3,593,422 | 7/1971 | Jankelson | 433/214 |
| 3,620,219 | 11/1971 | Barker | 128/791 |
| 3,659,614 | 5/1972 | Jankelson | 128/791 |
| 3,709,228 | 1/1973 | Barker | 128/791 |
| 3,722,099 | 3/1973 | Jankelson | 433/34 |
| 3,746,004 | 7/1973 | Jankelson | 128/791 |
| 3,797,500 | 3/1974 | Porter | 128/422 |
| 3,810,457 | 5/1974 | Bottcher et al. | 128/741 |
| 3,822,694 | 7/1974 | Mills | 433/63 |
| 3,851,651 | 12/1974 | Icenbice, Jr. | 128/422 |
| 3,902,502 | 8/1975 | Liss et al. | 128/422 |
| 3,946,745 | 3/1976 | Hsiang-Lai et al. | 128/421 |
| 3,983,881 | 10/1976 | Wickham | 128/421 |
| 4,014,347 | 3/1977 | Halleck et al. | 128/422 |
| 4,018,218 | 4/1977 | Carlson et al. | 128/1 C |
| 4,019,519 | 4/1977 | Geerling | 128/422 |
| 4,084,595 | 4/1978 | Miller | 128/422 |
| 4,147,171 | 4/1979 | Greene et al. | 128/421 |
| 4,174,706 | 11/1979 | Jankelson et al. | 128/741 |
| 4,305,402 | 12/1981 | Katims | 128/741 |
| 4,340,063 | 7/1982 | Maurer | 128/421 |
| 4,431,000 | 2/1984 | Butler et al. | 128/421 |

FOREIGN PATENT DOCUMENTS 2736345  2/1979  Fed. Rep. of Germany ...... 128/421

OTHER PUBLICATIONS

Myo–Monitor Model J3 instruction manual.

*Primary Examiner*—William E. Kamm
*Assistant Examiner*—Mitchell J. Shein
*Attorney, Agent, or Firm*—Andrus, Sceales, Starke & Sawall

[57] ABSTRACT

An electrical muscle stimulator (1) simultaneously supplies a pulse (i.e., 270, 271) to each electrode (5, 6) having first and second phases (272, 273; 274, 275) which are a mirror image to the pulse supplied to the other electrode. A control is connected to unbalance either or both the width and amplitude of the first and second phases of each pulse to selectively provide an unbalanced stimulation to one or more muscles through the electrodes (5, 6). The stimulator provides a precise control which is readily adjustable for a large number of operating sequences.

18 Claims, 21 Drawing Figures

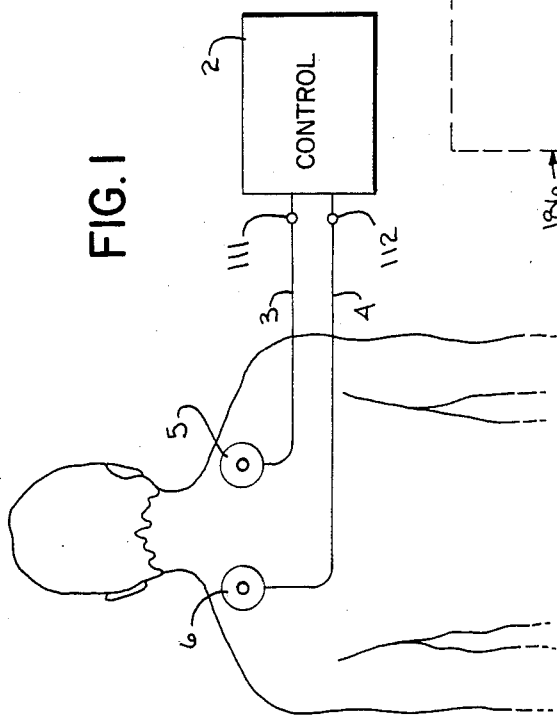
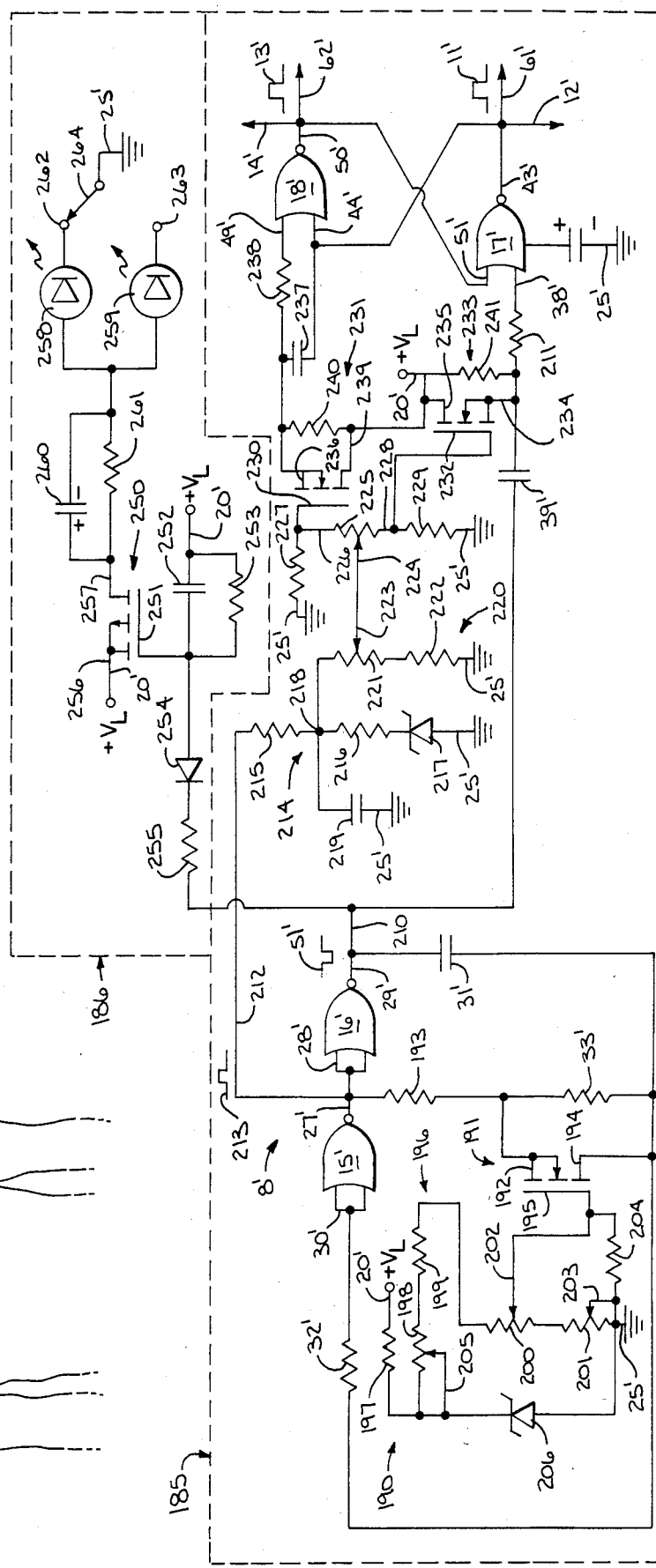

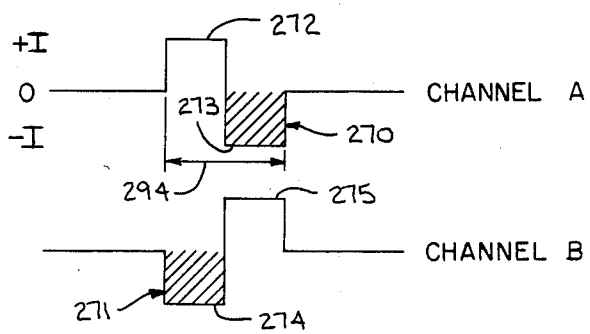
FIG. 5A
FIG. 5B
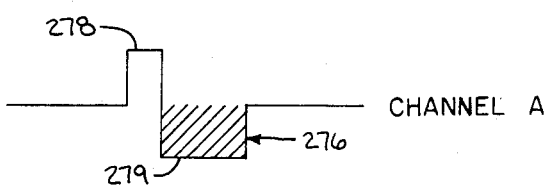
FIG. 5C
FIG. 5D
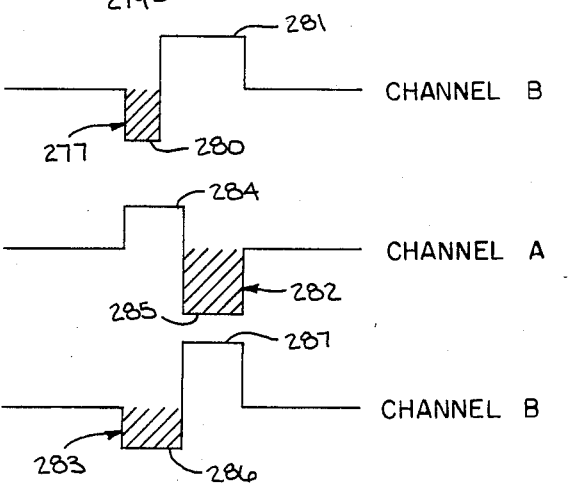
FIG. 5E
FIG. 5F
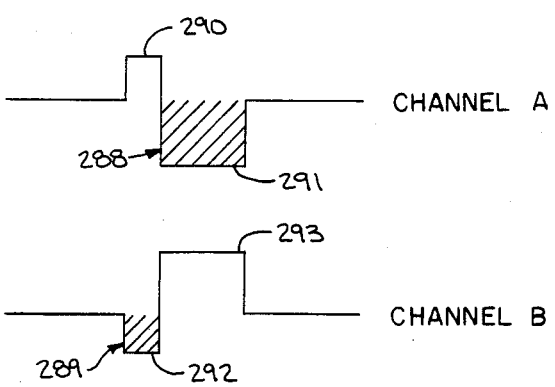
FIG. 5G
FIG. 5H

ELECTRICAL MUSCLE STIMULATOR

TECHNICAL FIELD

This application relates to a device to stimulate one or more muscles through an electrode attached to a body.

BACKGROUND OF THE INVENTION

The stimulation of muscles through electrical energy either directly to the muscles or to nerve fibers controlling such muscles has been found to be extremely desirable in a number of applications. Transcutaneous Electrical Nerve Stimulators (TENS) have been used to relax muscles and to diagnose and correct orthopedic problems. Further, electrical stimulation has been used to diagnose muscle responses in relaxation or contracture and to reduce swelling and discoloration through muscle contraction. Electrical stimulation has also been used to treat Myo-facial Pain Disfunction Syndrome (MPD) and Temporomandibular Joint Syndrome (TMJ). Selected muscle stimulation in the facial areas has been used to cause the closure of the mandible to determine the vertical position of occlusion and/or to take dental impressions. These and other applications presently used or to be used in the future are readily applicable to the electrical muscle stimulator.

Many prior muscle stimulators have required three or more electrodes with one electrode functioning as a dispersal electrode to achieve a balanced response of two or more muscles or groups of muscles, such as disclosed in U.S. Pat. No. 4,084,595; 3,983,881; 4,174,706 and and 3,797,500. Other systems have provided separation between fore and aft pulses in a dual electrode system and provide pulse separators for adjusting the time interval between pulses of opposite polarity in pairs of pulses, such as disclosed in U.S. Pat. No. 3,946,745.

SUMMARY OF THE INVENTION

The invention relates to a device to stimulate one or more muscles through one or more electrodes attached to the body. Such muscle stimulation may be accomplished directly, or through the stimulation of one or more nerves associated with such muscle.

A pulse source is electrically connected to simultaneously supply a bi-polar pulse to each of two electrodes having first and second phases which are a mirror image of the pulse supplied to the other electrode. A circuit is connected to the pulse source to differentially unbalance the first and second phases to selectively provide unbalanced stimulation to one or more muscles through the electrodes.

The widths of the first and second phases of the pulses may be differentially varied to provide an unbalanced response by one or more muscles. The amplitudes of the first and second phases may also be differentially varied to provide an unbalanced response by one or more of the muscles.

A first pulse generator provides a first pulse output while a second pulse generator is operatively connected to the first pulse generator and provides a second pulse output in response to the first pulse output. A summing circuit operatively combines the first and second pulse outputs to provide a combined pulse which operatively controls the supply of electricity to an electrode to stimulate one or more muscles. The electricity supplied to the electrode will include a first portion which is responsive to the first pulse output and a second portion which is responsive to the second pulse output. A combined pulse including the first and second portions may be selectively varied to unbalance the electricity supplied to the electrode.

A current transformer provides a primary winding which is coupled to a secondary winding connected to selectively supply a pulse to an electrode. A first switch is connected in circuit with the primary winding to control the duration of the pulse while a second switch is connected in circuit with the primary to control the amplitude of the pulse. The control provides a control signal which is operatively connected to simultaneously control the operation of the first and second switches to supply the pulse to the electrode. Four switches are connected in circuit in a bridge configuration and are selectively controlled to supply a pulse to each electrode having first and second phases which are a mirror image of the pulse supplied to the other electrode. The controlled switches in the bridge configuration control the pulse duration and may be operated in an unbalanced mode to provide unbalanced stimulation to one or more muscles. The amplitude controlling switch operates in two distinct phases for each output pulse to control the amplitude during the first and second phases thereof.

A signaling circuit is operatively connected to respond to the control signal to provide a visual indication signaling the supply of a pulse to an electrode.

The control has been particularly constructed to provide unbalanced stimulation to one or more muscles by unbalancing the first and second phases of each pulse supplied to an electrode. Where two electrodes are used, the first and second phases of each pulse supplied to a particular electrode are the mirror image of the pulse supplied to the other electrode.

Many additional novel features are found in the particular construction and operation as set forth in the drawings and the following description thereof as well as in the claims annexed hereto.

BRIEF DESCRIPTION OF THE DRAWINGS

FIG. 1 is a diagramatic view illustrating the connection of two electrodes and associated control to a body to stimulate one or more muscles;

FIGS. 5A-5I show a series of current wave forms illustrating possible outputs of the control to the electrodes illustrated in FIG. 1; and FIG. 6 is an electrical circuit schematic showing an alternative circuit construction for portions of the circuits illustrated in FIGS. 2 and 4.

DESCRIPTION OF THE PREFERRED EMBODIMENTS

Figure 2:
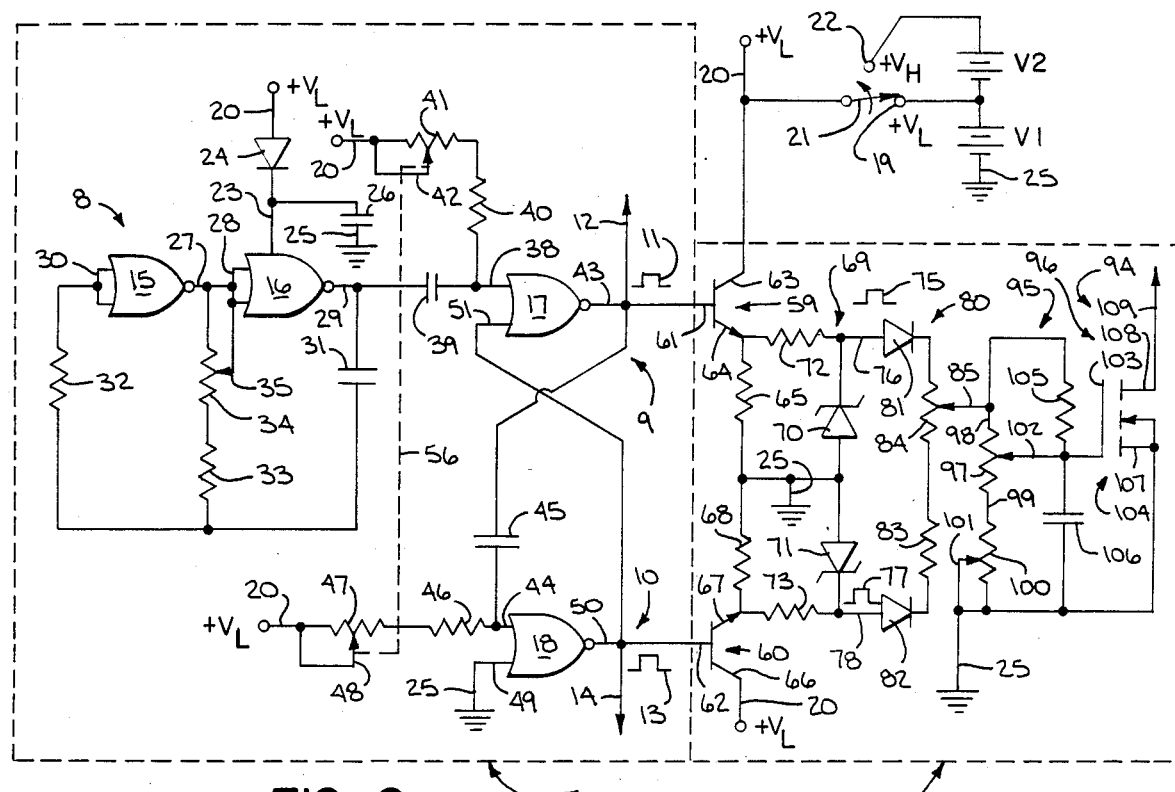
FIG. 2 is an electrical circuit schematic showing a portion of the control of FIG. 1.

An electrical muscle stimulator 1 includes a control 2 which is connected through a pair of leads 3 and 4 to a pair of electrodes 5 and 6, respectively. FIG. 1 illustrates the placement of electrodes 5 and 6 on the outer skin of a human body, with electrode 5 placed on the right shoulder while electrode 6 is placed on the left shoulder. With such placement, electrical signals are supplied by control 2 to electrodes 5 and 6 to electrically stimulate the right and left shoulders by stimulating the trapezius muscles located in the shoulders. Such stimulation might be provided directly to the trapezius muscles or, as more commonly understood, through the stimulation of nerves associated with such muscles.

While the embodiments set forth herein illustrate the connection of the electrodes 5 and 6 to the shoulder areas to stimulate the trapezius muscles, it is understood that the electrodes 5 and 6 could be placed on other locations of the body to stimulate other muscles for a desired response.

A pulse generating circuit 7 includes an astable multivibrator 8 connected to two monostable multivibrators 9 and 10 to provide a first pulse signal 11 at an output 12 and a second pulse signal 13 at an output 14.

The pulse forming circuit 7 includes the logic NOR circuit elements 15, 16, 17 and 18, which can be commercially purchased under the designation CD4001BE, such as provided by RCA in their quad two input NOR gate package. DC operating power can be provided from one or more conventional batteries. A battery V1 illustrated in FIG. 2 provides an output at terminal 19 to provide a substantially constant DC voltage signal $V_L$ at circuit 20 when switch 21 is operated to contact terminal 19. If desired, a second battery $V_2$ can be added in series with battery $V_1$ to provide a substantially constant higher voltage signal $V_H$ at terminal 22. The constant voltage signal $V_L$ is supplied to an input 23 of the NOR gate package through a diode 24 which is also connected to the system neutral or ground 25 through a stabilizing capacitor 26.

An output 27 of NOR 15 is connected to both inputs 28 of NOR 16 while an output 29 of NOR 16 is connected to both inputs 30 of NOR 15 through a series connected capacitor 31 and resistor 32. The output 29 of NOR 16 is also connected to its input 28 through the capacitor 31, a resistor 33 and a variable potentiometer 34 having a movable tap 35 which is electrically connected to input 28. In operation, the NOR elements 15 and 16 and associated circuits operate as an astable multivibrator to provide an oscillating output having a wave form approximating a square wave. The frequency of the output pulses supplied at 29 is established by the selection of the circuit components 3-34. The movable tap 35 of potentiometer 34 may be selectively adjusted to vary the frequency of the periodic pulses appearing at output circuit 29.

The NOR circuit 17 has a first input 38 connected to the output 29 of NOR 16 through a timing capacitor 39. The input 38 is also connected to the DC voltage signal $V_L$ through a resistor 40 and a variable potentiometer 41 having a movable tap 42. An output 43 of NOR 17 is connected to the output 12 and is also connected to an input 44 of NOR 18 through a timing capacitor 45. The input 44 is also connected to the constant DC voltage $V_L$ through a resistor 46 and a variable potentiometer 47 having a movable tap 48. An input 49 of NOR 18 is connected to the system neutral or ground 25 while an output 50 of NOR 18 is connected to an input 51 of NOR 17. The output 50 of NOR 18 is also connected to the output 14.

Figure 3A:
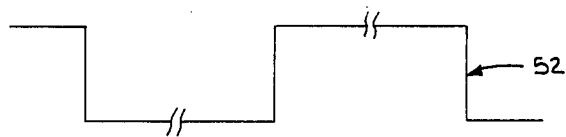
FIGS. 3A-3I show a series of wave forms illustrating various signals provided by the circuit of FIG. 2.
Figure 3B:
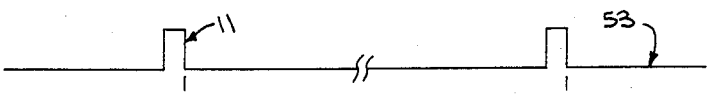
Figure 3C:
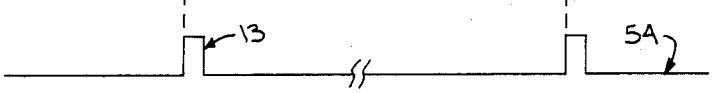

In operation, the astable multivibrator 8 functions to provide a substantially square wave signal at output 29 similar to that as illustrated by wave form 52 in FIG. 3A. The monostable multivibrator 9 responds to wave form 52 and provides a wave form 53 at output 12. The monostable multivibrator 10, in turn, responds to wave form 53 and provides a wave form 54 at output 14. As illustrated in FIGS. 3A–3C, the pulse 11 of wave form 53 is initiated on the negative going portion of wave form 52. Pulse 13 of wave form 54, on the other hand, is initiated on the downward going portion of pulse 11.

The tap 42 of variable potentiometer 41 can be selectively adjusted to vary the width of pulse 11 by varying the time constant of the RC circuit provided by capacitor 39 and resistors 40 and 41. In like manner, tap 48 of adjustable potentiometer 47 can be selectively adjusted to vary the width of pulse 13 by varying the time constant of the RC circuit including capacitor 45 and resistors 46 and 47. The taps 42 and 48 of potentiometers 41 and 47, respectively, are mechanically linked or interrelated as illustrated at 56 so that increasing the resistance of one potentiometer correspondingly decreases the resistance of the other potentiometer, and vice versa. In such manner, the increase of the pulse width of one pulse, such as pulse 11 for example, simultaneously decreases the width of the other pulse, such as pulse 13 for example.

A pulse control 58 is connected to respond to pulses 11 and 13 provided by outputs 43 and 50, respectively, of the pulse generator 7. A pair of NPN type transistors 59 and 60 function as buffer amplifiers with transistor 59 having a base circuit 61 connected to output 43 of NOR 17 while transistor 60 has a base circuit 62 connected to the output 50 of NOR 18. The transistor 59 has a collector circuit 63 connected to the constant DC voltage $V_L$ while an emitter circuit 64 is connected to the system neutral or ground 25 through a resistor 65. In like manner, transistor 60 has a collector 66 connected to the constant DC voltage $V_L$ while an emitter circuit 67 is connected to the system neutral or ground 25 through a resistor 68.

A voltage regulator 69 includes a pair of Zener diodes 70 and 71 and resistors 72 and 73. Specifically, the emitter circuit 67 of transistor 60 is connected to the system neutral or ground 25 through resistor 73 and Zener diode 71 while the emitter circuit 64 of transistor 59 is connected to the system neutral or ground 25 through resistor 72 and Zener diode 70. In operation, a pulse 75 having a predetermined clamped magnitude appears at circuit 76 in response to pulse 11 while an immediately succeeding pulse 77 having a predetermined clamped magnitude appears at circuit 78 in response to pulse 13. The pulses 75 and 77 have the same clamped magnitude throughout the normal range of battery voltage with pulse 77 immediately following pulse 75. The width of pulse 75 may be equal to or different from the width of pulse 77 which is dependent upon the width of pulses 11 and 13, respectively.

The pulses 75 and 77 are supplied to a summing and magnitude unbalance control 80 which includes a pair of diodes 81 and 82, a fixed resistor 83 and a variable potentiometer 84 having a movable tap 85. In that pulse 13 is formed in response to the termination of pulse 11, the summation of pulses 75 and 77 at potentiometer 84 provides a combined pulse 86 at tap 85, as illustrated by wave form 87 in FIG. 3D. If tap 85 of potentiometer 84 is set to a balanced predetermined position, the combined pulse 86 will have a uniform amplitude as illustrated at 88 in FIG. 3D. The movement of tap 85 from the predetermined balanced position in a first direction will produce a combined pulse 86 having two predetermined magnitudes, as illustrated at 89 and 90 in FIG. 3F. The movement of tap 85 in a second opposite direction from the predetermined balanced position will produce a combined pulse 86 with two predetermined amplitudes, as illustrated at 91 and 92 at FIG. 3H.

An amplitude control 94 responds to the combined pulse 86 at tap 85 and includes an adjustable magnitude control 95 coupled to a controlled impedance circuit 96. Specifically, a variable potentiometer 97 provides one lead 98 connected to the tap 85 and another lead 99 connected to the system neutral or ground 25 through a variable potentiometer 100. The potentiometer 100, in turn, provides a variable tap 101 which is coupled to the system neutral or ground 25. The potentiometer 97 provides a variable tap 102 which is connected to a gate electrode 103 of a field effect transistor circuit (FET) 104 operating as a variable impedance element. The gate 103 of FET 104 is also connected to tap 85 through a resistor 105 and is also coupled to the system neutral or ground 25 through a capacitor 106. In operation, the tap 101 of potentiometer 100 is adjusted to establish a threshold voltage for the conduction of the FET 104. The tap 102, in turn, is set to provide a desired amplitude for the combined pulse 86.

When the positive going combined pulse appears at gate circuit 103, the field effect transistor (FET) 104 is rendered conductive thereby completing a circuit path between the source 107 and the drain 108 which, in turn, is connected to the output circuit 109. The field effect transistor (FET) 104 is operated as a variable impedance device and will control the magnitude of the current flow at output circuit 109 in response to the magnitude of the voltage appearing at gate circuit 103.

Figure 3D:
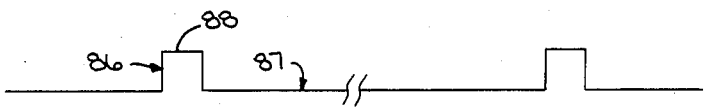
Figure 3E:
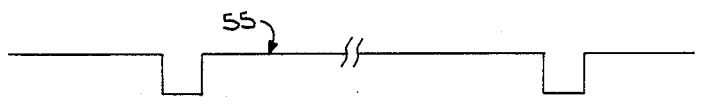
Figure 3F:
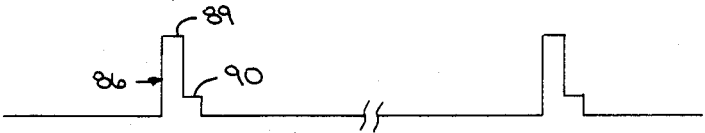
Figure 3G:
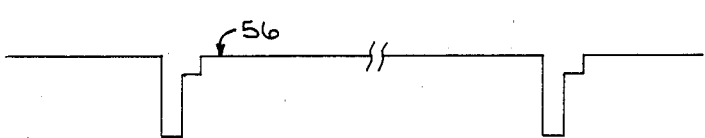
Figure 3H:
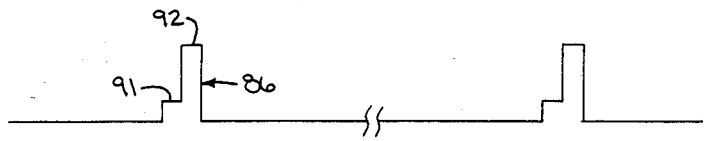
Figure 3I:
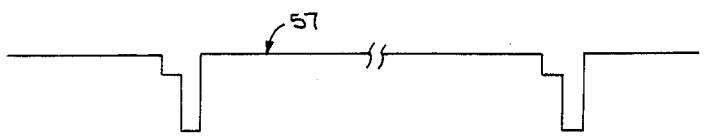

FIG. 3E illustrates an output 55 of FET 104 in response to the balanced combined pulse illustrated in FIG. 3D. FIG. 3G illustrates an output 56 of FET 104 in response to the unbalanced combined pulse illustrated in FIG. 3F. FIG. 3I illustrates an output 57 of FET 104 in response to the unbalanced combined pulse illustrated in FIG. 3H.

An output control circuit 110 provides output terminals 111 and 112 which are connected to electrodes 5 and 6 through connecting leads 3 and 4, respectively. An output step-down current transformer 113 includes a secondary winding 114 having one lead 115 connected to output terminal 111 while a second lead 116 is connected to the output terminal 112 through a current limiting resistor 117. A stabilizing capacitor 118 is connected across the secondary winding 114 to suppress inductive spikes while a center tap 114a on the secondary winding 114 is coupled to the system neutral or ground 25. A primary winding 119 of the current transformer 113 is connected across a pair of output circuits 120 and 121 of a controlled bridge circuit 122. Four switches, such as field effect transistors (FETs) if desired, form the four legs of the bridge circuit 122 and function to couple a constant DC voltage source as at 123 through the primary winding 119 of transformer 113 to the coupling circuit 109 which, in turn, is connected to the field effect transistor circuit 104 described above with respect to FIG. 2.

A field effect transistor (FET) 124 is in one leg of the bridge circuit and connects the voltage source lead 123 to the output circuit 120. Specifically, a source circuit 125 of FET 124 is connected to the constant voltage lead 123 while a drain circuit 126 is connected to the output circuit 120. A gate circuit 127 of FET 124 is connected to the constant source lead 123 through a resistor 128 and to a collector circuit 129 of an NPN type transistor 130. A base circuit 131 of transistor 130 is connected to the output circuit 14 to receive pulse 13 through a resistor 132. An emitter circuit 133 of transistor 130 is coupled to the system neutral or ground 25.

Another leg of the bridge circuit includes a field effect transistor (FET) 135 which includes a source circuit 136 connected to the constant voltage circuit 123 and a drain circuit 137 connected to the output circuit 121. A gate circuit 138 of FET 135 is connected to the constant voltage circuit 123 through a resistor 139 and is also connected to a collector circuit 140 of an NPN type transistor 141. The transistor 141, in turn, provides a base circuit 142 which is connected to circuit 12 to receive the pulse 11 through a resistor 143. An emitter circuit 144 of transistor 141 is coupled to the system neutral or ground 25.

The bridge circuit further includes a field effect transistor (FET) 145 in another leg which includes a source circuit 146 connected to the connecting circuit 109 while a drain circuit 147 is connected to the output circuit 120. A gate circuit 148 of FET 145 is connected to output circuit 12 to receive the pulse 11 and is also coupled to the system neutral or ground 25 through a stabilizing capacitor 149. The last leg of the bridge circuit also includes a field effect transistor (FET) 150 which provides a source circuit 151 which is connected to the coupling circuit 109 and a drain circuit 152 which is connected to the output circuit 121. A gate circuit 153 of FET 150 is connected to the output circuit 14 to receive pulse 13 and is also coupled to the system neutral or ground 25 through a stabilizing capacitor 154.

In operation, the FETs 124, 135, 145 and 150 operate as low impedance switches to selectively control the time periods when current will be conducted through the primary winding 119 of the current transformer 113 to provide output current pulses to electrodes 5 and 6. The occurrence of pulse 11 at base 142 will render transistor 141 conductive to provide a negative pulse 160 at the gate circuit 138 to thereby render the FET 135 conductive. The pulse 11 also appears at gate 148 to render FET 145 likewise conductive. The combined pulse 86 at tap 85 is, in part, responsive to pulse 11 and controls the magnitude of current flowing through FET 104 and thus in connecting circuit 109. A pulse conducting circuit path is established by the simultaneous conduction of FETs 104, 135 and 145 to conduct a pulse of conventional current in the direction indicated by arrow 161 through the primary 119 of transformer 113. The magnitude of such conducting current pulse is established by the amount of conduction of FET 104 in response to the magnitude of the first portion of the combined pulse 86.

The pulse 13, which is derived in response to the termination of pulse 11, is applied to base 131 to render transistor 130 conductive to provide a negative going pulse 162 which, in turn, gates FET 124 into conduction. The pulse 13 is also applied to gate 153 to render FET 150 conductive. The combined pulse 86 is, in part, derived from pulse 13 and renders FET 104 conductive during the time that FETs 124 and 150 are conductive in response to pulse 13. With FETs 104, 124 and 150 conductive, current passes in the direction of arrow 163 through primary 119 of transformer 113, the magnitude of which will depend upon the amount of conduction provided by FET 104 in response to the second portion of the combined pulse 86.

Figure 4:
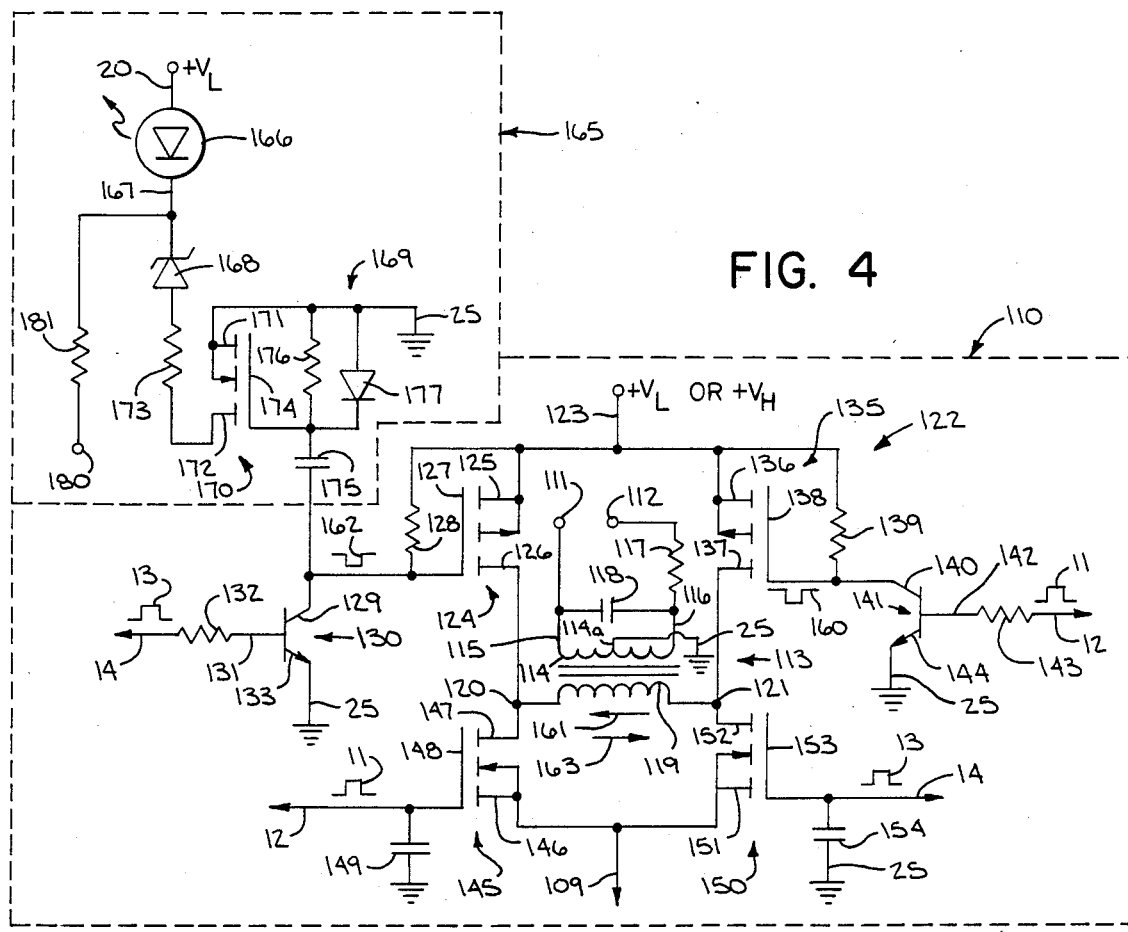
FIG. 4 is an electrical circuit schematic showing a portion of the control of FIG. 1.

A signaling circuit 165 is connected to provide a visual indication of the occurrence of electrical pulses. As illustrated in FIG. 4, a light emitting diode 166 has one circuit lead connected to the constant voltage circuit 20 and another lead 167 connected to the collector circuit 129 of the transistor 130 through a Zener diode 168 and a pulse stretching circuit 169. A field effect transistor circuit (FET) 170 provides a source circuit 171 connected to the system neutral or ground 25 and a drain circuit 172 connected to the anode of the Zener diode 168 through a resistor 173. A gate circuit 174 of FET 170 is connected to the collector circuit 129 of transistor 130 through a coupling capacitor 175. A parallel connected resistor 176 and diode 177 are connected between the gate 174 and the source 171 of the FET 170.

In operation, the FET 170 operates as a variable resistance and combines with the capacitor 175 to establish an extended conduction of FET 170 in response to pulse 162 to allow sufficient energization of LED 166 to permit visually observation of the LED 166 indicating the occurence of pulses 162. Specifically, the FET 170 is gated into conduction by the positive going trailing edge of pulse 162 to enable LED 166 to be energized following the pulse 162 to avoid current drain on the battery as current pulses are being supplied to electrodes 5 and 6. The Zener diode 168 causes the LED 166 to stop indicating the occurrence of pulses 162 when the battery voltage drops below a predetermined minimum valve. A test terminal 180 is connected to diode 166 through a resistor 181 and may be selectively grounded to determine whether LED 166 is operational.

FIG. 6 shows an alternative pulse generating circuit 185 and an alternative or additional pulse signaling circuit 186 which can be used in conjunction with the pulse control 58 illustrated in FIG. 2 and the output control circuit 110 illustrated in FIG. 4. Similar or substantially identical elements of the alternative circuit of FIG. 6 will be identified by identical numbers primed and further discussion of the function and operation thereof is deemed unnecessary.

A frequency modifying circuit 190 includes a field effect transistor (FET) 191 having a source circuit 192 connected to the juncture between the output 27' of NOR 15' and inputs 28' of NOR 16' through a resistor 193. A drain circuit 194 of FET 191 is connected to the output 29' of NOR 16' through capacitor 31' and is also connected to the inputs 30' of NOR 15' through the resistor 32'. A gate circuit 195 of FET 191 is coupled to the constant voltage source circuit 20' through a voltage dividing network 196. Specifically, the constant voltage source circuit 20' is connected to the system neutral or ground 25' through a fixed resistor 197, a variable potentiometer 198, a fixed resistor 199, a variable potentiometer 200 and a variable potentiometer 201. A variable tap 202 of potentiometer 200 is connected to the gate circuit 195 to provide a selectable gate signal for controlling the degree of conduction by FET 191. A tap 203 of potentiometer 201 provides a threshold voltage for gate 195 to establish a minimum frequency. A fixed resistor 204 reduces the gate input impedance of FET 191. A movable tap 205 of potentiometer 198 provides additional voltage control to establish a maximum frequency while a Zener diode 206 provides a clamp to regulate the voltage appearing at the tap 205 of potentiometer 198.

In operation, the FET 191 operates as a variable resistance to selectively control the operating frequency of the pulses generated by the NOR circuits 15' and 16'. Such frequency can be selectively varied by the adjustment of any of the taps 202, 203 or 205 which, in turn, varies the degree of conduction by FET 181 to effectively vary the impedance in the feedback circuit.

An output circuit 210 is connected to the output 29' of NOR 16' and supplies the train of pulses 51' to the input 38' of NOR 17' through the coupling capacitor 39' and an input resistor 211. Another output circuit 212 is connected to the output 27' of NOR 15' and supplies a train of pulses 213 which are one hundred and eighty degrees (180°) out of phase from the output 51'. The signal 213 is supplied to a voltage clamping circuit 214 featuring a series circuit including resistors 215 and 216 and Zener diode 217, the latter having an anode circuit connected to the system neutral or ground 25'. A junction 218 between resistors 215 and 216 is coupled to the system neutral or ground 25' through a stabilizing capacitor 219.

A variable pulse width control 220 includes a variable potentiometer 221 which is coupled to the system neutral or ground 25' through a resistor 222. The potentiometer 221 has one lead connected to the juncture 218 to receive the clamped pulses 213. A movable tap 223 of potentiometer 221 is connected to a movable tap 224 of a potentiometer 225. The potentiometer 225 has one circuit lead 226 connected to the system neutral or ground 25' through a resistor 227 while another circuit lead 228 is connected to the system neutral or ground 25' through a resistor 229. The circuit 226 of potentiometer 225 is also connected to a gate 230 of a field effect transistor (FET) 231 while the circuit 228 of potentiometer 225 is connected to a gate 232 of a field effect transistor (FET) 233. A source circuit 234 of FET 233 is connected to input 38' of NOR 17' through resistor 211 while a drain circuit 235 is connected to the constant voltage circuit 20'. A source circuit 236 of FET 231 is connected to input 44' of NOR 18' through a capacitor 237 and is also connected to input 49' of NOR 18' through a resistor 238. A drain circuit 239 of FET 231 is connected to the constant voltage source circuit 20'. A voltage dropping resistor 240 is connected across the source and drain circuits of FET 231 while a voltage dropping resistor 241 is connected across the source and drain circuits of FET 233.

In operation, FETs 231 and 233 function as variable resistances through the controlled conduction thereof in response to the pulses 213 as modified by the adjustment of variable taps 223 and 224. By varying the effective resistance displayed by FET 233, the time constant provided in association with capacitor 39' and resistor 241 is changed to vary the response of NOR circuit 17' to pulse 51'. By varying the resistance provided by FET 231, the time constant of capacitor 237 and resistor 240 is modified to likewise vary response of NOR circuit 18' to the output pulse 11' NOR 17'. The selective adjustment of tap 223 of potentiometer 221 thus varies the pulse width of pulses 11' and 13'. By moving tap 223 in one direction, the width of the pulses 11' and 13' will become longer while moving tap 223 in the opposite direction will have the inverse effect by making the width of pulses 11' and 13' shorter. Movement of the tap 224 will vary the symmetry between pulses 11' and 13'. Thus movement of tap 224 in one direction will make one of the pulses 11' and 13' longer while the other pulse will be correspondingly shorter. Movement of tap 224 in the opposite direction will have the inverse results.

The pulse signaling circuit 186 includes a field effect transistor (FET) 250 having a gate circuit 251 connected to the constant voltage source circuit 20' through a parallel connected capacitor 252 and resistor 253. The gate circuit 251 is also connected to the output circuit 210 through a serially connected diode 254 and resistor 255. A source circuit 256 of FET 250 is connected to the constant voltage circuit 20' while a drain circuit 257 is connected to a pair of light emitting diodes (LEDs) 258 and 259 through a parallel connected capacitor 260 and resistor 261. A cathode of diode 258 is connected to a switch contact 262 while cathode circuit of diode 259 is connected to a switch contact 263. A selectively movable switch arm 264 is connected to the system ground or neutral 25' and is selectively movable between contacts 262 and 263 to selectively insert LEDs 258 or 259 into circuit operation.

In operation, the FET 250 responds to the negative going pulse 51' and becomes conductive to supply an energizing circuit through one of the LEDs 258 or 259 to provide a visual indication responsive to the occurrence of pulse 51'. The resistive capacitive combination 252 and 253 provide an extended conduction for LEDs 258 or 259 following the occurrence of pulse 51' in order to have a satisfactory visual indication. The parallel connected capacitor 260 and resistor 261 allow greater current to flow through LED 258 or 259 at lower frequencies than at higher frequencies to thereby maintain the apparent brightness at a substantially constant level during all frequencies and to conserve power at high frequencies.

If desired, switch arms 21 and 264 may be ganged together for simultaneous operation so that the connection of switch arm 21 with circuit 19 for operation under voltage V1 will simultaneously connect LED 258 into circuit. When switch arm 21 is positioned to supply a higher voltage V2 at contact 22, the LED 259 would be connected in circuit. In such manner, an operator could visually determine which voltage was being used for a particular sequence of operation.

The FETs illustrated in the circuit schematics may be selected from any commercially available source and could be of the type sold under the designations VP0300M and VN0300M, by Siliconix as Vertical MOS Power FETs.

The current wave forms shown in FIGS. 5A through 5H illustrate various operating sequences of system operation. FIGS. 5A, 5C, 5E and 5G are labeled Channel A meaning that such current wave forms are supplied to electrode 5 through output terminal 111 and connecting circuit 3 while the current wave forms labeled Channel B in FIGS. 5B, 5D, 5F and 5H are supplied to electrode 6 through output terminal 112 in connecting lead 4.

The current outputs illustrated in FIGS. 5A–5H have the negative going phase shaded to emphasize negative phase stimulation. It is believed that muscles or the nerves that control such muscles are stimulated to a much higher degree by the negative going phase of a bi-polar pulse whereas the positive going phase provides a lesser stimulus.

FIGS. 5A and 5B illustrate a balanced sequence of operation wherein a balanced current pulse 270 is supplied to the Channel A electrode 5 and a balanced current pulse 271 is supplied to the Channel B electrode 6. In such sequence, the tap 224 of potentiometer 225 is located at a balanced position so that the width of pulse portion 272 is equal to the width of pulse portion 273. If the circuit of FIG. 2 is being utilized, the taps 42 and 48 of potentiometers 41 and 47, respectively, are located at a balanced position to provide a balanced pulse width.

Further, the tap 85 of potentiometer 84 is located at a balanced position so that the amplitude of pulse portion 272 is equal but opposite to the amplitude of the pulse portion 273. The pulse portion 273 is always immediately adjacent to pulse portion 272 and both portions 272 and 273 form a combined bi-polar current pulse with two phases equal in magnitude and pulse width. In that taps 224 [or taps 42 and 48 in FIG. 2] and 85 are at a balanced position, the current pulse 271 is inversely related to the current pulse 270. Thus, the pulse portion 274 is a mirror image of pulse portion 272, i.e. of opposite polarity. The pulse portion 275 is likewise the mirror image of pulse portion 273, i.e. of opposite polarity.

Frequently, in diagnostics and/or medical treatment, it is desirable to submit an unequal or unbalanced response to one or more muscles to effectuate an unbalanced stimulation. Such unbalanced stimulation is provided by either unbalancing the width of the pulse portions or unbalancing the amplitudes of the pulse portions, or unbalancing both the width and amplitude of the pulse portions.

FIGS. 5C and 5D illustrate an unbalanced width of current pulses 276 and 277 which are supplied to electrodes 5 and 6, respectively. In such situation, the tap 85 is maintained at a balanced position while tap 224 is moved to an unbalanced position [taps 42 and 48 would be unbalanced if FIG. 2 were used] resulting in pulse portion 278 having a substantially smaller width than pulse portion 279. The pulse portion 280 of the current pulse 277 is the mirror image of pulse portion 278, i.e. of the opposite polarity. In like manner, the pulse portion 281 of the current pulse 277 is a mirror image of pulse portion 279, i.e. but of opposite polarity. The current pulses 276 and 277 provide an unequal response by providing an unbalanced width of the pulse portions therein. An increase in the width of pulse portions 279 and 281 will likewise cause a corresponding decrease in the width of pulse portions 278 and 280, respectively, and vice versa. The increasing of pulse portion 279 and the simultaneous decreasing of pulse portion 280 increases the stimulation at channel A while decreasing the stimulus at channel B thereby providing an unbalanced response to the muscles.

The current pulses 282 and 283 in FIGS. 5E and 5F illustrate current pulses with balanced pulse widths but unbalanced amplitudes. In such situation, the tap 224 is located at a balanced position [taps 42 and 48 would be balanced if FIG. 2 were used] to provide equal widths of pulse portions 284 and 285. The tap 85, however, is located at an unbalanced position so that the amplitude of pulse portion 285 is greater than pulse portion 284. In like manner, the pulse portion 286 is of lesser magnitude than of the pulse portion 287 and pulse portions 286 and 287 are mirror images of pulse portions 284 and 285, respectively. An increase in current amplitude of pulse portions 284 and 286 will likewise cause a corresponding decrease in the current amplitude of pulse portions 285 and 287, respectively, and vice versa. By making the pulse portion 285 larger in amplitude than pulse portion 286, an increase in stimulation will be supplied to channel A while a decrease in stimulation will result at channel B thereby producing in an unbalanced condition.

The current pulses 288 and 289 in FIGS. 5G and 5H illustrate an operation providing an unbalance in width and amplitude of the pulse portions. In such situation, the taps 224 [taps 42 and 48 would be unbalanced if FIG. 2 were used] and 85 are both located at unbalanced positions so to provide an unbalanced width and an unbalanced amplitude of the pulse portions. For example, the pulse portion 290 of pulse 288 is less in width and magnitude than the pulse portion 291. The pulse portion 292 of pulse 289 is a mirror image of pulse portion 290 while pulse portion 293 is a mirror image of pulse portion 291, i.e. of opposite polarities. The unbalanced current pulses 288 and 289 thus provide an unbalanced stimulation to one or more muscles through electrodes 5 and 6 by presenting an unbalance in width and amplitude of the pulse portions. making the pulse portion 291 larger in amplitude and width than pulse portion 292, an increase in stimulation will be supplied to channel A while a decrease in stimulation will result at channel B thereby producing an unbalanced condition.

The overall width 294 of each bi-polar current pulse, such as pulse 270 in FIG. 5A for example, can be selectively varied by adjusting tap 223 of potentiometer 221, while each portion (i.e., 272, 273) will remain at a constant relative width as determined by tap 224 of potentiometer 225. Further, the amplitude of both pulse portions can be selectively varied in a uniform manner by adjusting tap 102 of potentiometer 97.

The use of a single bi-polar pulse supplied in mirrored form to the electrodes 5 and 6 permit the use of the electrical muscle stimulator with as few as two electrodes under balanced and unbalanced conditions. The two portions of each bi-polar pulse can be varied in width or amplitude, or both, to provide the desired unbalanced stimulation to the muscle or groups of muscles.

Various modes for carryiny out the invention are contemplated as being within the scope of the following claims particularly pointing out and distinctly claiming the subject matter which is regarded as the invention.

I claim:

1. A device to stimulate one or more muscles through first and second electrodes attached to a body, comprising
    a pulse source electrically connected to said first and second electrodes to simultaneously supply a bipolar pulse to each electrode having first and second phases which are a mirror image of the pulse supplied to the other electrode, and
    means connected to said pulse source for differentially unbalancing said first and second phases to selectively provide unbalanced stimulation to one or more muscles through said first and second electrodes.

2. The device of claim 1, wherein said unbalance means includes
    means for differentially varying the widths of said first and second phases to provide an unbalanced response by said one or more muscles.

3. The device of claim 2, wherein said varying means includes
    means for differentially varying the amplitudes of said first and second phases.

4. The device of claim 1, wherein said unbalance means includes
    means for differentially varying the amplitudes of said first and second phases to provide an unbalanced response by said one or more muscles.

5. The device of claim 1, wherein said unbalance means includes
    means for differentially varying the widths and amplitudes of said first and second phases to provide an unbalanced response by said one or more muscles.

6. A device to stimulate one or more muscles through an electrode attached to a body, comprising
    a first pulse generator providing a first pulse output and a second pulse generator operatively connected to said first pulse generator and providing a second pulse output in response to the termination of said first pulse output,
    means operatively connected for summing the magnitudes of said first and second pulse outputs to provide a combined pulse, and
    means operatively connected to said summing means and to said electrode for selectively supplying electricity to said electrode in response to said combined pulse to stimulate one or more of said muscles.

7. The device of claim 6, wherein said electricity supplying means includes
    means for supplying a pulse to said electrode having a first portion responsive to said first pulse output and a second portion responsive to said second pulse output.

8. A device to stimulate one or more muscles through an electrode attached to a body, comprising
    means for providing first and second control signals with said second signal being produced in response to said first signal terminating,
    means for combining said first and second control signals to provide a combined signal having a first portion responsive to said first control signal and a second portion responsive to said seocnd control signal, an
    means operatively connected to said combining means and said electrode for selectively supplying electricity to said electrode in response to said first and second portions of said combined signal.

9. The device of claim 8, and including
    means for varying said first portion of said combined signal to unbalance said electricity supplied to said electrode.

10. The device of claim 8, and including
    means for varying the amplitude of said first and second portions of said combined signal to vary the amplitude of said electricity supplied to said electrode.

11. A device to stimulate one or more muscles through an electrode attached to a body, comprising
    control means for providig first and second control signals with said second signal being produced in response to said first signal terminating, and
    means for supplying electrical energy to said electrode including a first energy portion responsive to said first control signal and a second energy portion response to said second control signal to stimulate one or more of said muscles.

12. A device to stimulate one or more muscles through an electrode attached to a body, comprising
    a current transformer having a primary winding coupled to a secondary winding connected to selectively supply a pulse to said electrode,
    first switching means including a first switch connected in circuit with said primary winding for controlling the duration of said pulse,
    second switching means including a second switch connected in circuit with said primary winding for controlling the amplitude of said pulse, and
    control means providing a control signal operatively connected for simultaneously controlling the operation of said first and second switching means to supply said pulse to said electrode.

13. The device of claim 12, wherein
said first switch controls the duration of a first portion of said pulse, and
said first switching means includes a third switch connected in circuit with said primary winding to control the duration of a second portion of said pulse.

14. The device of claim 13, wherein
said second switch provides a first response to control the current amplitude during the first portion of said pulse and a second response to control the current amplitude during the second portion of said pulse.

15. The device of claim 12, wherein
said first switching means includes third, fourth and fifth switches connected in circuit with said primary winding for controlling the duration of said pulse, with said first, third, fourth and fifth switches connected in a bridge configuration and said control means providing a plurality of control signals to control the operation of said first, third, fourth and fifth switches.

16. The device of claim 12, and including
pulse signaling means operatively connected to respond to said control signal for providing a visual indication signaling the supply of said pulse to said electrode.

17. A device to stimulate one or more muscles through first and second electrodes attached to a body, comprising
a pulse generating source including an astable multivibrator providing a pulse train,
a first monostable multivibrator having an input connected to respond to said pulse train to provide a first pulse output,
a second monostable multivibrator having an input connected to receive said first pulse output of said first monostable multivibrator to provide a second pulse output which is directly responsive to the said first pulse output,
pulse modifying circuit including a first variable impedance providing an input to said first monostable multivibrator and a second variable impedance providing an input to said second monostable multivibrator with said first and second variable impedances selectively adjustable between a balanced position and a plurality of unbalanced positions to differentially vary the widths of said first and second pulse outputs,
a pulse control connected to said pulse generating source and including
first and second buffer amplifiers connected to respond to said first and second pulse outputs, respectively,
first and second voltage regulators connected to said first and second buffer amplifiers, respectively, to provide first and second clamped output pulses in response to said first and second pulse outputs, respectively,
a summing and magnitude unbalance control circuit including a third variable impedance connected to said first and second voltage regulators to receive said first and second clamped pulses, respectively, and providing an adjustable output to provide a combined pulse in direct response to said first and second clamped pulses,
an amplitude control including an adjustable magnitude control providing a fourth variable impedance connected to said adjustable output of the third variable impedance of said summing and magnitude unbalance control circuit and providing an adjustable output to select between a balanced condition and a plurality of unbalanced positions for supplying balanced and unbalanced combined pulses and
a controlled impedance including a first field effect transistor having a gate circuit connected to said adjustable output of said fourth variable impedance and having an output circuit providing a current output signal directly proportional to said combined pulse, and
an output control circuit including
a controlled bridge circuit including second, third, fourth and fifth field effect transistors each forming a leg of the bridge circuit and providing first and second input terminals formed between said second and third and between said fourth and fifth field effect transistors, respectively, with said first input terminal connected to said output circuit of said controlled impedance provided by said pulse control and said second input terminal connected to an energy source, and further providing first and second output terminals formed between said second and fourth and between said third and fifth field effect transistors respectively, said second and fifth field effect transistors connected to respond to said first pulse output and said third and fourth field effect transistors connected to respond to said second pulse output, and
an output current transformer having a primary connected across said first and second output terminals and a secondary electrically connected to said first and second electrodes to supply a pulse to each electrode having positive and negative portions which are a mirror image of the pulse supplied to the other electrode to selectively provide balanced and unbalanced stimulation to one or more muscles through said first and second electrodes.

18. The device of claim 17, wherein said astable multivibrator includes
a first logic element providing a first pulse train and
a second logic element connected to respond to the first pulse train and provide a second pulse train and
a frequency modifying circuit coupling said first and second pulse trains as inputs to said first logic element, said frequency modifying circuit including a sixth field effect transistor having a gate circuit connected to a second energy source through a fifth variable impedance which is selectively adjusted to provide a predetermined conduction of said sixth field effect transistor for selecting the frequency of said first and second pulse trains,
said first monostable multivibrator connected to respond to said second pulse train to provide said second pulse output, and
said pulse modifying circuit including a sixth variable impedance having an input connected to respond to said first pulse train and an output connected to said first monostable multivibrator through a seventh variable impedance including a seventh field effect transistor and connected to said second monostable multivibrator through an eighth variable impedance including an eighth field effect transistor, said sixth variable impedance selectively adjustable between a balanced position and a plurality of unbalanced positions to differentially vary the widths of said first and second pulse outputs.

* * * * *